(12) United States Patent
Whiteside et al.

(10) Patent No.: US 10,456,198 B2
(45) Date of Patent: Oct. 29, 2019

(54) GUIDED WAVE ABLATION AND SENSING

(71) Applicants:Paul James Douglas Whiteside, Columbia, MO (US); Benjamin Samuel Goldschmidt, Columbia, MO (US); John A. Viator, Columbia, MO (US); Randy D. Curry, Columbia, MO (US); Nicholas J. Golda, Columbia, MO (US)

(72) Inventors: Paul James Douglas Whiteside, Columbia, MO (US); Benjamin Samuel Goldschmidt, Columbia, MO (US); John A. Viator, Columbia, MO (US); Randy D. Curry, Columbia, MO (US); Nicholas J. Golda, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 889 days.

(21) Appl. No.: 14/730,845

(22) Filed: Jun. 4, 2015

(65) Prior Publication Data
US 2015/0351841 A1 Dec. 10, 2015

Related U.S. Application Data

(60) Provisional application No. 61/997,549, filed on Jun. 4, 2014, provisional application No. 62/125,476, filed on Jan. 21, 2015.

(51) Int. Cl.
*A61B 18/20* (2006.01)
*G02B 6/42* (2006.01)
(Continued)

(52) U.S. Cl.
CPC .......... *A61B 18/203* (2013.01); *A61B 5/0095* (2013.01); *G02B 6/4206* (2013.01);
(Continued)

(58) Field of Classification Search
None
See application file for complete search history.

(56) References Cited

U.S. PATENT DOCUMENTS

| | | | |
|---|---|---|---|
| 8,512,322 B1* | 8/2013 | Liu | A61B 18/203 606/15 |
| 2004/0059399 A1* | 3/2004 | Neuberger | A61N 5/062 607/91 |

(Continued)

FOREIGN PATENT DOCUMENTS

EP 2 705 805 A1 3/2014

OTHER PUBLICATIONS

Kong et al., "High-Resolution Photoacoustic Imaging with Focused Laser and Ultrasonic Beams." Applied Physics Letters, 94, 2009. pp. 1-3.*

(Continued)

*Primary Examiner* — James M Kish
(74) *Attorney, Agent, or Firm* — Stinson LLP (57) ABSTRACT

Systems and methods for the controlled delivery of laser light to target tissue using an improved waveguide. A waveguide controls transmission of wave energy to a target based on direct contact with the target. The waveguide comprises a propagation medium, a cladding causing the electromagnetic wave to be internally reflected in the medium, and an interface formed in the cladding and configured for direct contact with the target. A portion of the laser light penetrates through the cladding at the interface and propagates into the target while a portion internally reflects within the propagation medium.

17 Claims, 7 Drawing Sheets

(51) Int. Cl.
   *A61B 5/00*    (2006.01)
   *A61B 18/00*   (2006.01)
(52) U.S. Cl.
   CPC ......... *G02B 6/4291* (2013.01); *G02B 6/4296* (2013.01); *A61B 2018/00005* (2013.01); *A61B 2018/00452* (2013.01); *A61B 2018/00577* (2013.01); *A61B 2018/00785* (2013.01)

(56) References Cited

U.S. PATENT DOCUMENTS

| | | | | |
|---|---|---|---|---|
| 2009/0156932 | A1* | 6/2009 | Zharov | A61B 5/0059 600/437 |
| 2011/0190749 | A1* | 8/2011 | McMillan | A61B 18/22 606/16 |
| 2014/0275826 | A1* | 9/2014 | Li | A61B 5/0095 600/301 |
| 2014/0276685 | A1* | 9/2014 | Gustavsson | A61B 18/203 606/9 |
| 2017/0065346 | A1* | 3/2017 | Weisberg | A61B 18/22 |

OTHER PUBLICATIONS

Choi, Choon-Gi et al., Two-dimensional polymeric optical waveguides for high-density parallel optical interconnection, Optics Communications 235 (2004) pp. 69-73.

Chua, Jeun Kee et al., Resonant amplification of frustrated evanescent waves by single dielectric coating, Optics Communications 283 (2010) pp. 169-175.

Court, Ian N. et al., Frustrated Total Internal Reflection and Application of its Principle to Laser Cavity Design, Applied Optics, vol. 3, No. 6, Jun. 1964, pp. 719-726.

Kullab, Hani M. et al., Transverse magnetic peak type metal-clad optical waveguide sensor, Optik 124 (2013) pp. 7080-7084.

Tien, P.K. et al., Theory of Prism-Film Coupler and Thin-Film Light Guides, Journal of the Optical Society of America, vol. 60, No. 10, Oct. 1970, pp. 1325-1337.

Zhu, Yu et al., Frustrated total internal reflection evanescent switching, Optics & Laser Technology 31 (1999) pp. 539-542.

Zourob, Mohammed et al., Metal clad leaky waveguides for chemical and biosensing applications, Biosensors and Bioelectronics 20 (2005) pp. 1718-1727.

Zourob, Mohammed et al, The development of a metal clad leaky waveguide sensor for the detection of particles, Sensors and Actuators B 90 (2003) pp. 296-307.

* cited by examiner

GUIDED WAVE ABLATION AND SENSING

CROSS-REFERENCE TO RELATED APPLICATIONS

This application claims priority to co-pending U.S. Provisional Application No. 62/125,476, filed Jan. 21, 2015, and U.S. Provisional Application No. 61/997,549 filed Jun. 4, 2014, the entire contents of which are incorporated herein by reference.

BACKGROUND

Currently available laser delivery techniques used for dermatology, such as for tattoo removal and medical laser ablation, typically operate in the UV, visible, or infrared spectra. Furthermore, current dermatological applications typically involve the propagation of waves using picosecond, nanosecond, microsecond, or millisecond pulse widths, and also involve continuous wave lasers. Often, a fiber optic bundle, articulated mirror system, or the like directs the laser light from a beam source into a hand-piece control unit positioned above the skin and aimed toward the target. This creates an area of free space (i.e., an air gap) between the hand-piece and the target. Because these procedures propagate a laser through free space to illuminate target tissue, they allow for a dangerous degree of electromagnetic energy to be released, both when the wave propagates in free space and when the propagated light reflects off of the target tissue. Under typical circumstances, even a diffuse reflectance of 1% of the transmitted wave into the eyes of an operator or patient is enough to cause permanent ocular damage.

In addition, conventional laser systems exhibit poor heat dissipation at the tissue-air interface. This can exacerbate the negative thermal effects at the tissue surface, which result in potentially drastic changes to the tissue being treated, diminishing overall effectiveness of the treatment, prolonging the time needed to recover between treatments, increasing the number of treatments required, etc. For example, excessive heat can damage or permanently scar the topmost layers of skin, reduce the efficacy of subsequent treatments, and even vaporize water within the tissue. In addition to damaging the target tissue, vaporizing water within the tissue increases the relative fat density at the surface, which causes even more back-scattered light to reflect from the tissue surface during treatment.

SUMMARY

Briefly, aspects of the present invention provide improved, controlled laser delivery and essentially eliminate the air gap between a hand-piece delivering laser light and target tissue. In this manner, aspects of the invention provide improved ablation and sensing particularly well-suited for dermatological applications. In an aspect, a waveguide controls transmission of wave energy to a target based on direct contact with the target. This results in improvements over conventional ablation and sensing techniques. Advantageously, by limiting transmission of a wave to when direct contact with a desired target medium occurs, aspects of the invention prevent propagation of the wave into free space and, thus, reduce the likelihood of injury. Additionally, a waveguide system embodying aspects of the invention provides for ablating tissue in custom geometries and over large surface areas. This results in improved techniques of laser delivery for various dermatological uses. For example, transmitting beams of comparatively lower power at increased frequency provides improved efficacy compared to conventional ablation techniques, reducing overall treatment costs for patients in applications such as tattoo removal procedures. Further, aspects of the invention permit greater sensitivity and a reduced signal to noise ratio compared with conventional techniques by detecting an acoustic response from the same side of a target as the side receiving the transmitted wave. Also, incorporating a detection component within a waveguide embodying aspects of the invention allows for sensing an acoustic response of greater intensity, without the risk of the detection component occluding generation of the resulting signal.

In an aspect, a system for controlling delivery of an electromagnetic wave to a target comprises a waveguide for receiving the electromagnetic wave from an electromagnetic source. The waveguide includes a propagation medium coupled to the source for receiving the electromagnetic wave from the source. The waveguide also includes a cladding on the propagation medium and an interface at the cladding configured for direct contact with the target. The cladding causes the electromagnetic wave to be internally reflected within the propagation medium and the wave propagates within the propagating medium when the refractive index at the interface is less than that of the propagation medium. A portion of the wave penetrates through the interface and propagates into the target when the interface is in contact with the target such that the refractive index at the interface is approximately the same as or greater than the refractive index of the propagating medium.

A method embodying aspects of the invention includes receiving, by a waveguide, an electromagnetic wave from an electromagnetic source. The waveguide includes a propagation medium coupled to the source for receiving the electromagnetic wave from the source. The waveguide also includes a cladding on the propagation medium and an interface at the cladding configured for direct contact with the target. The cladding causes the electromagnetic wave to be internally reflected within the propagation medium. The method further includes propagating the wave within the propagating medium when the refractive index at the interface of the target is less than that of the propagating medium and propagating at least a portion of the wave into the target by penetrating through the cladding when the interface is in contact with the target such that the refractive index at the interface is approximately the same as or greater than the refractive index of the propagating medium.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
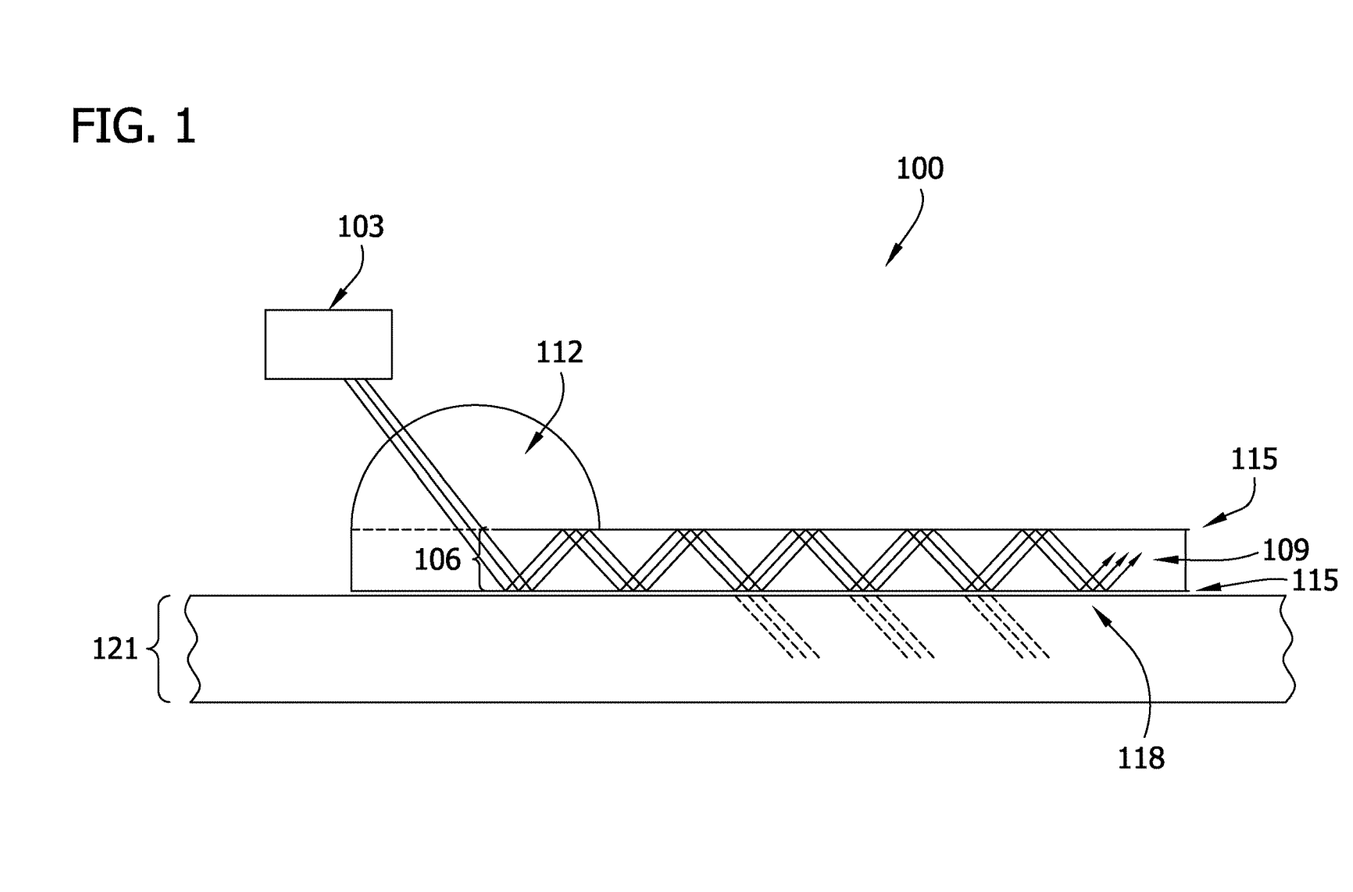
FIG. 1 illustrates an exemplary system including an interface configured for controlled delivery of an electromagnetic wave when in direct contact with a target according to an embodiment of the invention.

Referring now to the drawings, FIG. 1 illustrates an exemplary system for controlled delivery of an electromagnetic wave, including an interface configured for controlled delivery of the wave when the interface is in direct contact with a target (e.g., biological tissue) according to an embodiment of the invention. A system 100 comprises a source 103 for transmitting an electromagnetic wave through a waveguide 106 to achieve optical illumination of a target medium (e.g., target 121). In an embodiment, the source 103 produces an electromagnetic wave at laser energies suitable for medical uses, such as cosmetic surgery (e.g., to remove tattoos, scars, stretch marks, sunspots, wrinkles, birthmarks, spider veins, or hair), photoacoustic sensing, and the like. For example, source 103 uses controlled stimulated emission to produce electromagnetic radiation at wavelengths greater than 180 nm but less than or equal to $1.0 \times 10^6$ nm. In other words, the electromagnetic wave is laser light.

The waveguide 106 receives the electromagnetic wave from source 103 and further comprises a propagating medium 109, such as a planar slab of dielectric material. In an embodiment, the system 100 also includes a coupling lens 112 configured to receive the electromagnetic wave at various angles from the source 103. In one embodiment, the coupling lens 112 is hemicylindrical in shape and paired with an additional, similarly formed lens (not shown) to vary the angle of the received electromagnetic wave incident on the coupling lens 112 to determine the manner in which the wave is propagated within the propagating medium 109. In another embodiment, the system 100 is operated by transmitting an electromagnetic wave at a fixed angle such that the internal reflection angle of the electromagnetic wave results in total internal reflection (TIR). As an example, operating the system 100 to transmit a wave at a fixed angle is well-suited for use in clinical applications.

As shown in FIG. 1, the waveguide 106 includes a cladding 115 covering the propagating medium 109. In an embodiment, the lens pair, i.e., the coupling lens 112 paired with the additional lens, acts as a 1:1 Keplerian beam expander so that the electromagnetic wave transmitted as a beam remains collimated within the waveguide 106, and the lenses are refractive-index-matched to at least one of the propagating medium 109 and the cladding 115. For example, where dispersion within the waveguide 106 is desirable, a single lens is used as a coupling lens 112 and is not paired with the additional lens. In other embodiments, adjusting the internal reflection angle in accordance with material properties of the waveguide 106 optimizes energy delivery. Such properties comprise material parameters of waveguide 106 components, including an active area of the waveguide 106 as will be further described herein.

Referring further to FIG. 1, the cladding 115 that surrounds the propagating medium 109 comprises an interface 118 configured for direct contact with a target 121. In an embodiment, the coupling lens 112 paired with the additional lens is configured to receive the electromagnetic wave from source 103 and deliver it via the interface 118 at an internal reflection angle to optimize the energy delivery to the target 121 according to the material properties of waveguide 106.

The wave propagates within the propagating medium 109 and remains within the propagating medium 109 when the refractive index at the interface 118 is less than the refractive index of the propagating medium 109. On the other hand, the waveguide 106 is configured such that the received wave propagates within the propagating medium 109 and at least a portion of the wave exits the propagating medium 109 when the refractive index of the target 121 is greater than the refractive index of the cladding 115. In an embodiment, a cladding layer 115 does not surround the propagating medium 109, and the determination of whether a portion of the received wave exits the propagating medium 109 depends in part on the refractive index of the propagating medium 109 when compared to the refractive index of the target 121.

With further reference to FIG. 1, the waveguide 106 is configured based upon the properties of electromagnetic waves, which can be described as photons as well as waves. When the cladding 115 comprises a secondary material of lower refractive index compared to the propagating medium 109, the light internally reflects away from the interface 118 in much the same way that a particle would away from a boundary between the propagating medium 109 and the cladding 115. The light also exhibits a degree of penetration into the cladding 115, in the form of an exponentially decaying field of energy referred to as the evanescent field. In an embodiment, the evanescent field is absorbed within the cladding 115 where the cladding 115 is sufficiently thick. In another embodiment, the evanescent field is entirely reflected away from the interface 118 along with the remainder of the photon energy packet.

Advantageously, in an embodiment, cladding 115 is configured to be thinner than the penetration depth of the evanescent field at the interface 118. In this manner, the propagating wave comes into contact with the cladding 115, and the evanescent field penetrates the cladding 115, extending into the target 121 and forming a newly propagating within the target 121. The evanescent field is known to form a newly propagating wave in a similar manner in the event that the cladding 115 is optically absorbing. In an embodiment, the interface 118 of cladding 115 allows for the portion of the energy to penetrate into the target 121 in the event that the target 121 is in contact with interface 118 and has a refractive index that is greater than or equal to the refractive index of the propagating medium 109.

To illustrate using one non limiting example, if the interface 118 is in contact with target 121 and the target 121 has a refractive index greater than that of the propagating medium 109, a significant portion of the wave exits the propagating medium 109 and travel into the target 121 via the interface 118. In this manner, the system 100 comprises waveguide 106 configured such that upon direct physical contact of the interface 118 with target 121 (e.g., biological tissue), a portion of the propagated electromagnetic wave refracts into target 121, and a portion reflects within propagating medium 109 to continue to propagate within the waveguide 106. In one embodiment, the propagated electromagnetic wave partially penetrates the cladding 115 of the waveguide 106 at interface 118 through optical tunneling and propagates into the target 121. And the propagated electromagnetic wave partially reflects within propagating medium 109 to continue propagating within the waveguide 106. The direct-contact design of waveguide 106 at the interface 118 formed in the cladding 115 allows for the controlled release of electromagnetic energy thus reducing the possibility of ocular damage caused in conventional systems when the wave propagates in free space or reflects off of the target tissue.

In an embodiment, the source 103, the coupling lens 112, and the components comprising the waveguide 106 of the system 100 are configured such that the number of total internal reflection (TIR) points, the relative spacing between the points, and the respective internal reflection angle of the points determine wave propagation within the propagating medium 109. These characteristics also determine the extent to which the wave penetrates or tunnels through the cladding 115 at each of the TIR points where an evanescent field is formed by the energy of the incident wave slightly crossing the boundary between the two materials (i.e., interface 118). In an embodiment, the evanescent field is enhanced by configuring at least one of the following: the polarization of the incident wave, the internal reflection angle of the wave, the wavelength of the wave within the waveguide 106, the choice of material used for the cladding 115, the thickness of the cladding 115, and by forming patterns on the cladding 115 comprising apertures. In an embodiment, configuring the components in the manner described allows for an effect known as surface plasmon resonance (SPR) to cause a portion of the electric field at each TIR point to be transferred into the free-electron cloud of the cladding 115, subsequently resulting in an electric field that propagates along the exterior surface of the cladding 115, resulting in an enhanced evanescent field.

Figure 2:
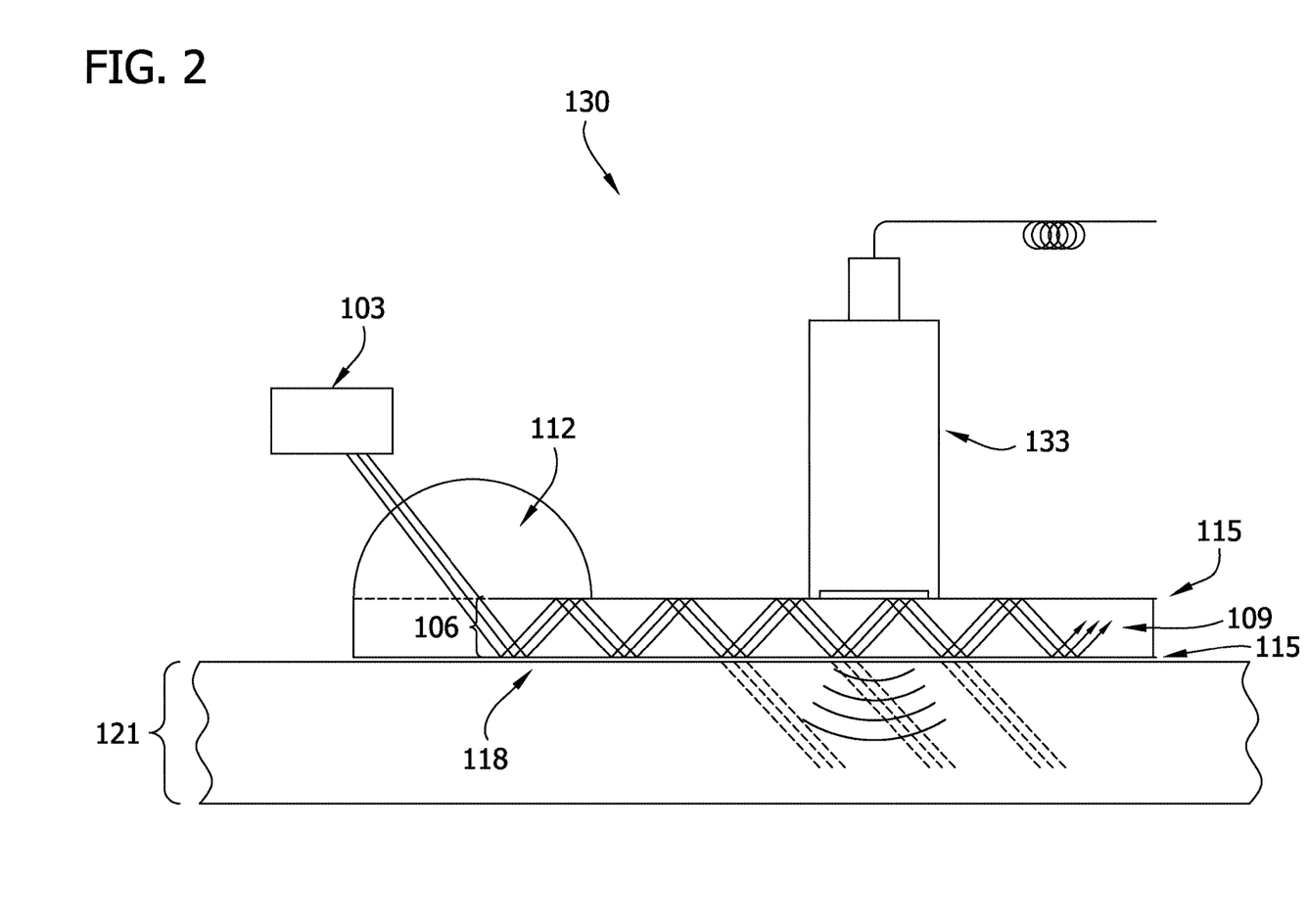
FIG. 2 illustrates an exemplary system, including an ultrasonic pulser, for controlled delivery of an electromagnetic wave for use in ablation according to an embodiment of the invention.

FIG. 2 illustrates an exemplary system 130 for the controlled delivery of an electromagnetic wave for use in ablation, according to an embodiment of the invention. The system 130 comprises source 103 and waveguide 106, which comprises propagating medium 109 for transmitting an electromagnetic wave through the waveguide 106. In the illustrated embodiment, coupling lens 112 determines the manner in which the wave is propagated within the propagating medium 109. The cladding 115 surrounds the propagating medium 109 and waveguide 106 is configured for controlled delivery of an electromagnetic wave when interface 118 is in direct contact with target 121.

According to aspects of the invention, the system 100 operates the source 103 to transmit an electromagnetic wave at an intensity level suitable for ablation. As is known in the art, a variety of interactions occur when the propagating wave (e.g., laser light) comes into contact with a boundary between the propagating medium 109 and the cladding 115 in a manner that results in TIR.

With further reference to FIG. 2, in an embodiment, the source 103 is further capable of emitting, for example, nanosecond-pulsed laser light at a wavelength of 532 nm to result in an improved photoacoustic response. In an embodiment, the target 121 comprises biological tissue, and the system 130 is configured to be applicable in medical laser ablation fields such as tattoo removal, tumor ablation, varicose vein reduction, port-wine-stain removal, and skin resurfacing. In another embodiment, the system 130 is configured for the application of pulsed laser light in procedures such as percutaneous tumor ablation. Additionally or alternatively, other components are used with the system 130, including contact cooling elements, electrodes, and imaging modalities.

In an embodiment, the system 130 further comprises an ultrasonic pulser 133 configured for receiving pulses from a pulse generator (not shown). The ultrasonic pulser 133 is capable of pulsing the target 121 at various ultrasonic frequencies. For example, in the event that the target 121 comprises biological tissue, the ultrasonic pulser 133 is capable of creating micro-bubbles of gas within the target by introducing ultrasonic pulses into the target 121. By incorporating the ultrasonic pulser 133 into the system 130, the gas bubbles generated by the pulser 133 alter the optical properties of the target 121 in various ways, such as by decreasing the bulk absorption of the target 121, and by decreasing the scattering coefficients of the target 121.

As demonstrated by FIG. 2, the direct-contact design of the waveguide 106, which includes the interface 118 formed in cladding 115, allows for the incident wave to propagate within the propagating medium 109 at the area of the target 121 being treated by the ultrasonic pulser 133, and prevents the ultrasonic pulser 133 from occluding the path of the wave as the wave travels within the propagating medium 109. Moreover, system 130 allows for the ultrasonic pulser 133 to be used in a manner not available with free-space propagation techniques. In an embodiment, the use of ultrasonic pulser 133 allows for increased penetration depth of the wave, resulting in propagation of the wave within the target 121 in a manner that would otherwise not be possible with traditional methods of illumination, since an ultrasonic pulser would occlude the path of the laser light in a conventional laser ablation system. Moreover, increasing the penetration depth of the wave greatly enhances the effectiveness of procedures such as medical laser ablation.

Figure 3:
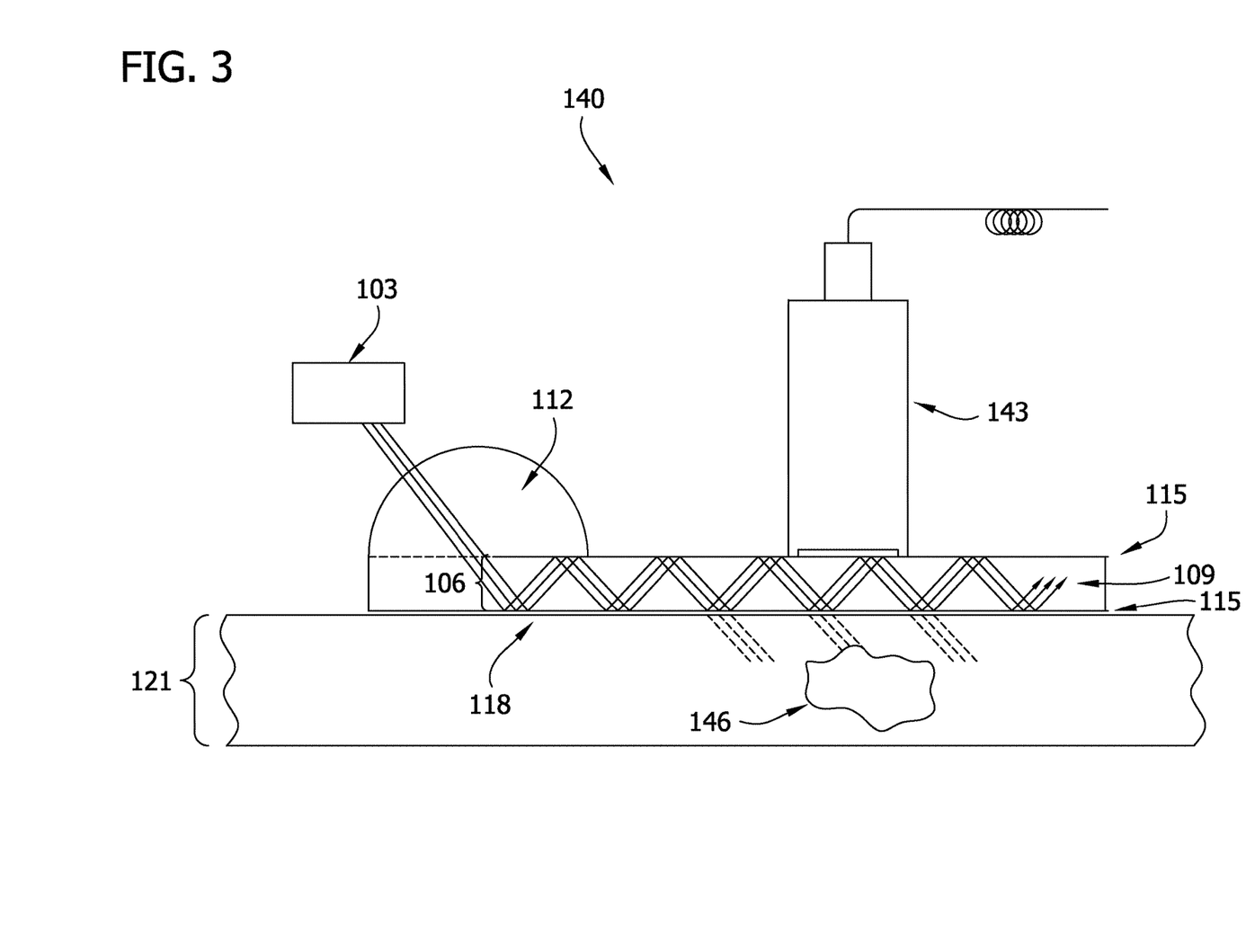
FIG. 3 illustrates an exemplary system, including an ultrasonic sensor, for controlled delivery of an electromagnetic wave for use in sensing photoacoustic signals generated within a target according to an embodiment of the invention.

FIG. 3 illustrates an exemplary system 140 for the controlled delivery of an electromagnetic wave for use in sensing photoacoustic signals generated within the target 121 according to an embodiment of the invention. The system 140 includes source 103 and coupling lens 112. The source 103 is configured to transmit the wave to waveguide 106 using the coupling lens 112 as described above. The waveguide 106 comprises propagating medium 109 for transmitting an electromagnetic wave through the waveguide 106. And cladding 115 surrounds the propagating medium 109. The interface 118 of cladding 115 is configured for controlled delivery of the wave to the target 121 when the interface 118 is in direct contact with target 121 as described above. In an embodiment, the system 140 is configured such that the intensity level of the electromagnetic wave is suitable for detecting the backward-mode of photoacoustic waves incited in the target 121.

With further reference to FIG. 3, the system 140 is advantageously configured to permit the design of various system components in geometries that allow for other sensing modalities to be incorporated in close proximity to the site of controlled delivery of electromagnetic wave energy to the target 121. Specifically, the direct-contact design of the system 140 allows for enhanced detection by providing various sensing modalities without occluding the wave delivered to the target 121. In an embodiment, system 140 is configured to detect the photoacoustic response in target 121 resulting from absorbing electromagnetic energy from the source 103. In an embodiment, a sensing modality (see ultrasonic sensor 143) is incorporated behind the waveguide 106 of system 140, and this sensing modality provides for illumination of target 121 by allowing incited photoacoustic signals to be received on the same side of the target 121 as the generated source signals. The sensed signals are based upon signals generated by the source 103 and propagated into the target 121 when the interface 118 is in direct contact with target 121 having sufficient refractive index. As appreciated by those skilled in the art, different materials have different photoacoustic properties. For example, damaged biological tissue exhibits a different photoacoustic response than healthy tissue. The sensed signals are received after the signals propagated into the target 121 come into contact with material having photoacoustic properties that are distinct from the surrounding tissue of target 121, such as distinct target material 146. Propagated signals that contact the distinct target material 146 incite distinct photoacoustic signals in comparison to the responses incited in the target 121 surrounding distinct target material 146.

Still referring to FIG. 3, system 140 further comprises a sensing modality such as a photoacoustic detector. In one non-limiting example, the photoacoustic detector comprises an ultrasonic sensor 143. In an embodiment, the ultrasonic sensor 143 is duplicated in various combinations in an array, and is incorporated onto the back surface of the waveguide 106 to detect photoacoustic signals reflected from within the target 121. In an embodiment, the ultrasonic signals detected by the sensor 143 are detected along the same axis as the signal generated by the source 103 and propagated into the target 121. In an embodiment, the functionality provided by the capability of detecting the incited signals along the same axis as the source signal allows for the computational reconstruction of a three-dimensional map of distinct target material 146 within the target 121. In an embodiment, the computationally reconstructed map is based on signals incited from the distinct target material 146. In an embodiment, the reconstructed map is generated by using the array of sensing modalities to scan an area of interest by receiving the incited photoacoustic responses. The system 140 provides for the generation of a three-dimensional image, in that the optical properties of abnormal tissue result in distinct photoacoustic responses compared to those of normal tissue, applicable in areas such as severe burn depth analysis, cancerous tumor detection, and vasculature imaging.

In an additional embodiment, the cladding 115 is an optically transparent polymer and the system 140 includes a suitable camera for monitoring laser ablation in real time. Real time laser ablation monitoring includes, for example, computationally scaling the energy delivered based on observed optical properties of the target 121 and the distinct target material 146 within the target 121. In another embodiment, real time laser ablation monitoring includes computationally tracking previously delivered energy to prevent overexposure of delivered energy to the target 121. As one non-limiting example, such an embodiment provides for sensing the depth of tattoo ink, as well as the ink used, which varies greatly depending on many factors. By providing a device such as system 140 capable of visualizing various ink properties, treatment dosage is adjustable to a greater degree, resulting in improved efficacy and decreased overall treatment cost.

Additionally or alternatively, sensing modalities are provided in front of the waveguide 106. In one non-limiting example, with further reference to FIG. 3, a sample is placed between the waveguide 106 and the target 121, and the evanescent field that results as the wave reflects at the TIR point is partially absorbed by the sample. In an embodiment, configuring the system 140 to emit pulsed laser light causes absorption by the sample that results in a photoacoustic response that is detectable by the sensor 143, due to the relation between the wavelength of the light incident upon the cladding 115 and the penetration depth of the evanescent field into the cladding 115. For example, the sample is a molecule or biological target and chemical or biological agents can be incorporated onto the waveguide 106 to enhance the photoacoustic response incited in the sample. In another embodiment, a microfluidic flow cell is constructed on the waveguide 106 to enable the detection of particular samples, or enable the detection of particular chemical or biological agents used to adhere to the sample. In yet another embodiment, an application-specific waveguide with a sensing modality provided in front of the waveguide is fabricated as a readily replaceable sensing chip.

In additional embodiments, the waveguide 106 is configured for fabrication in various applications; non-limiting examples include disease detection and monitoring (e.g., melanoma, malaria), gas sensing (e.g., explosive analyte detection), or crop ripeness determinations (e.g., farm crops or vineyards). In another embodiment, the waveguide 106 is configured with a sensing modality provided in front of the waveguide 106 for use as a Total Internal Reflection Photoacoustic Spectroscopy (TIRPAS) resonator, advantageous in that the incorporation of additional TIR points compounds the amplitude of the resultant photoacoustic wave. In part due to this compounded amplitude, the waveguide 106 configured as a TIRPAS resonator allows for the optical and geometric properties of thin films to be determined with an improved signal-to-noise ratio in comparison with conventional TIRPAS techniques. In addition to the applications described above, the system 140 of FIG. 3 as well the system 130 of FIG. 2 provide improved techniques of laser delivery in various treatment areas; a list of non-limiting examples includes: Plastic and Reconstructive Surgery, Urology, Obstetrics and Gynecology, Oral and Maxillofacial Surgery, Ophthalmology, Otolaryngology, Cardiology, and Orthopaedic Surgery.

Figure 4:
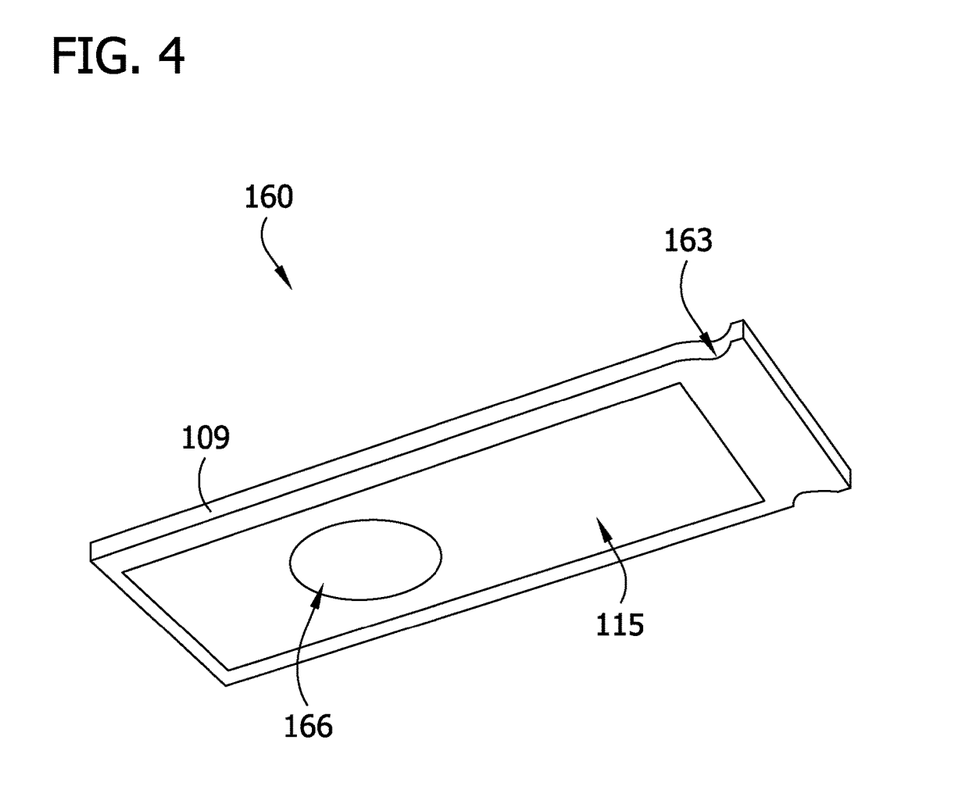
FIG. 4 illustrates an exemplary optical waveguide apparatus having a cladding and an active area therein for use in the systems of FIGS. 1-3.

FIG. 4 illustrates an exemplary optical waveguide apparatus 160 for the controlled delivery of an electromagnetic wave according to an embodiment of the invention. The exemplary optical waveguide apparatus comprises a waveguide 106 that is configured for controlling the delivery of an electromagnetic wave to a target, such as target 121, based in part on the materials selected for fabricating the waveguide 106. As depicted in FIG. 4, waveguide 106 includes propagating medium 109 covered by cladding 115. In an embodiment, the propagating medium 109 comprises a plastic or glass microscope slide, further comprising notches 163 for locking the waveguide apparatus 160 in place when it is used in a system (such as system 140, or system 180 described herein) for sensing photoacoustic signals generated within a target. Additionally, cladding 115 includes an active area 166 scaled to control the energy of the wave that propagates into the target 121. The active area 166 is characterized, in an embodiment, by a comparatively thin section of the cladding 115, such that the evanescent field penetrates through the active area 166 into a target 121 with increased intensity as compared to the cladding 115, which is coated in a comparatively thick cladding 115 that inhibits energy loss. In an embodiment, the active area 166 forms a circular shape (e.g., 1 inch in diameter) on the surface of the cladding 115. Additionally or alternatively, the active area 166 forms a rectangular shape in the cladding 115. It is to be understood that active area 166 can be different sizes depending on design considerations and usage. In an alternative embodiment, the waveguide apparatus 160 forms a curved shape to optimize direct contact between the waveguide 166 and the target.

As described above, active area 166 is formed by areas of masked off sections of the propagating medium 109 such that the cladding 115 is subsequently formed on the propagating medium 109 to adhere to the propagating medium 109 and does not form on the active area 166. After adhering the cladding 115 to the propagating medium 109, the masked off areas are removed from the active area 166. In an embodiment, thin films are subsequently deposited on the active areas 166. In another embodiment, the thin films comprise the material used for the cladding 115. In another embodiment, the active area 166 is comprised of at least one of the following: silver, titanium, or molybdenum. In an embodiment, active area 166 and cladding 115 are formed of the same material, and the thickness of active area 166 is comparatively less than the thickness of cladding 115, thereby allowing the evanescent field formed by the internal reflection of the propagated wave to penetrate into target 121.

Figure 5:
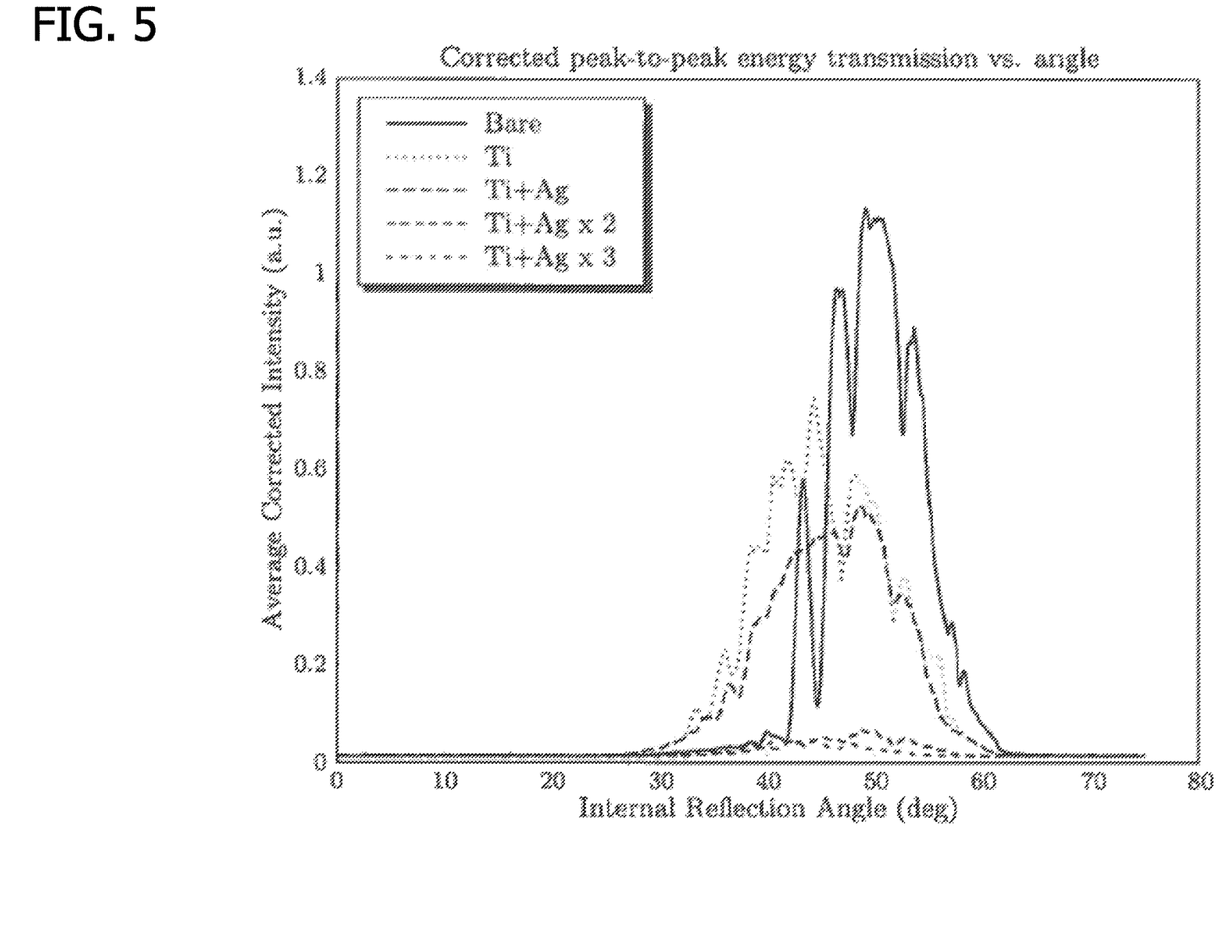
FIG. 5 graphically depicts the effect of adding various materials to the active area of the waveguide apparatus of FIG. 4 on energy transmission through the active area.

FIG. 5 illustrates the effect of adding layers of various materials to the active area 166 upon energy transmission through the active area of an optical waveguide apparatus, such as waveguide apparatus 160, using the system of FIG. 3. FIG. 5 shows the photoacoustic response of a source configured to vary the internal reflection angle of a propagated wave across a range. The average corrected intensity (in arbitrary units) of energy transmitted through active area 166 of waveguide apparatus 160 decreases when layers of silver are added to the active area 166. As described herein, the decrease in energy transmission is additionally based upon the low refractive index of silver, as well as on other factors. In contrast, average corrected intensity is made more efficient when layers of titanium are added to a bare active area, in part based upon the comparatively high refractive index of titanium.

Figure 6:
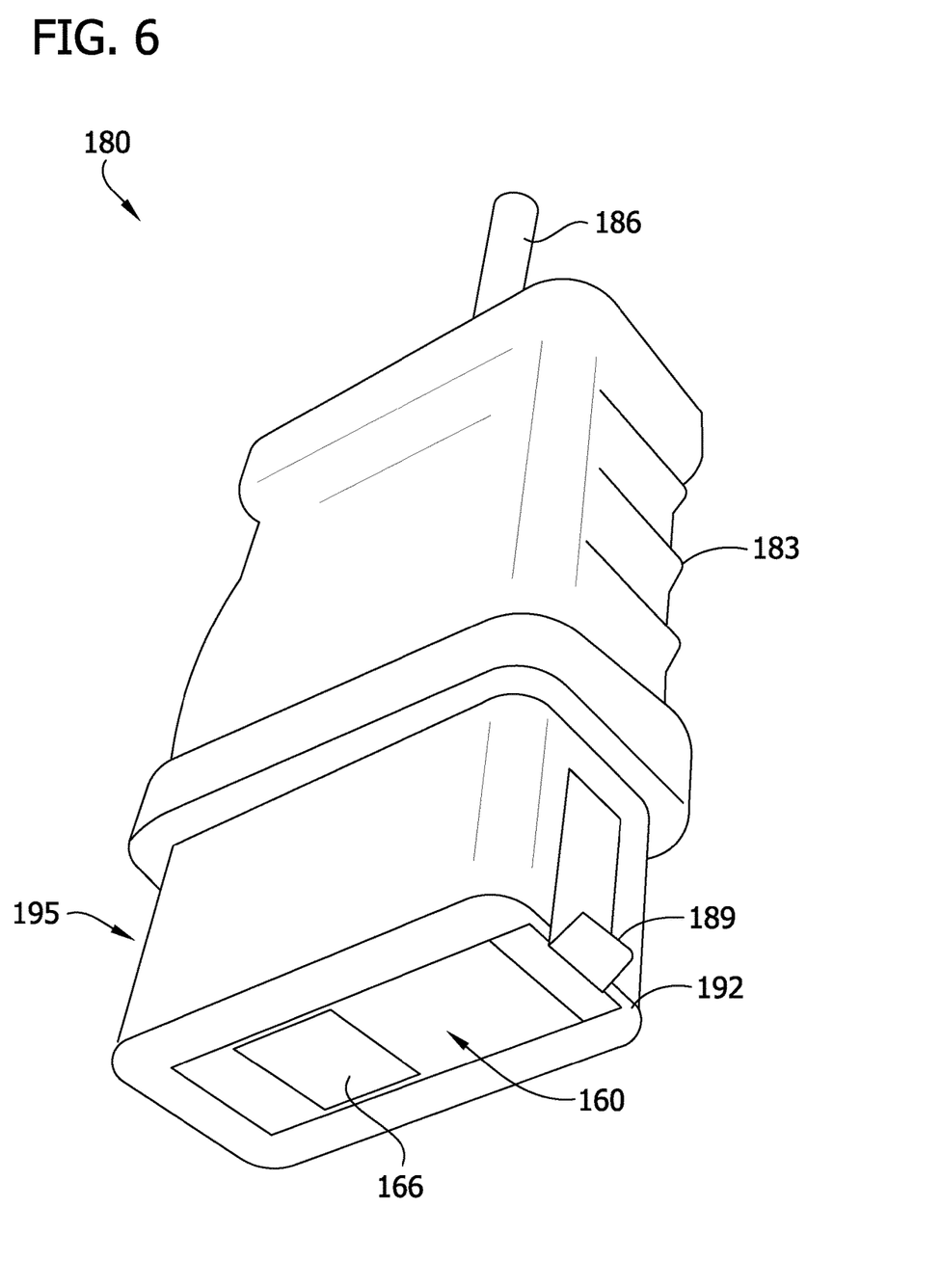
FIG. 6 illustrates a handheld apparatus including an optical waveguide for use with the systems of FIGS. 1-3.

FIG. 6 illustrates an exemplary handheld unit 180 for the controlled delivery of an electromagnetic wave according to an embodiment of the invention. The handheld unit 180 comprises a rubber hand grip 183, a cable 186 further comprising an optical fiber, as well as a slide lock 189 and slide grooves 192. The slide lock 189 and slide grooves 192 are configured for accepting a waveguide (such as waveguide apparatus 160) comprising a polymer, sapphire, or glass microscope slide, further comprising notches (such as notches 163) for locking the waveguide in place. The housing 195 surrounds and encloses the unit 180. In an embodiment, the housing 195 further comprises additional components uses in ablation and sensing, such as contact cooling elements, electrodes, and imaging modalities. Additionally or alternatively, housing 195 surrounds and encloses the additional components.

Figure 7:
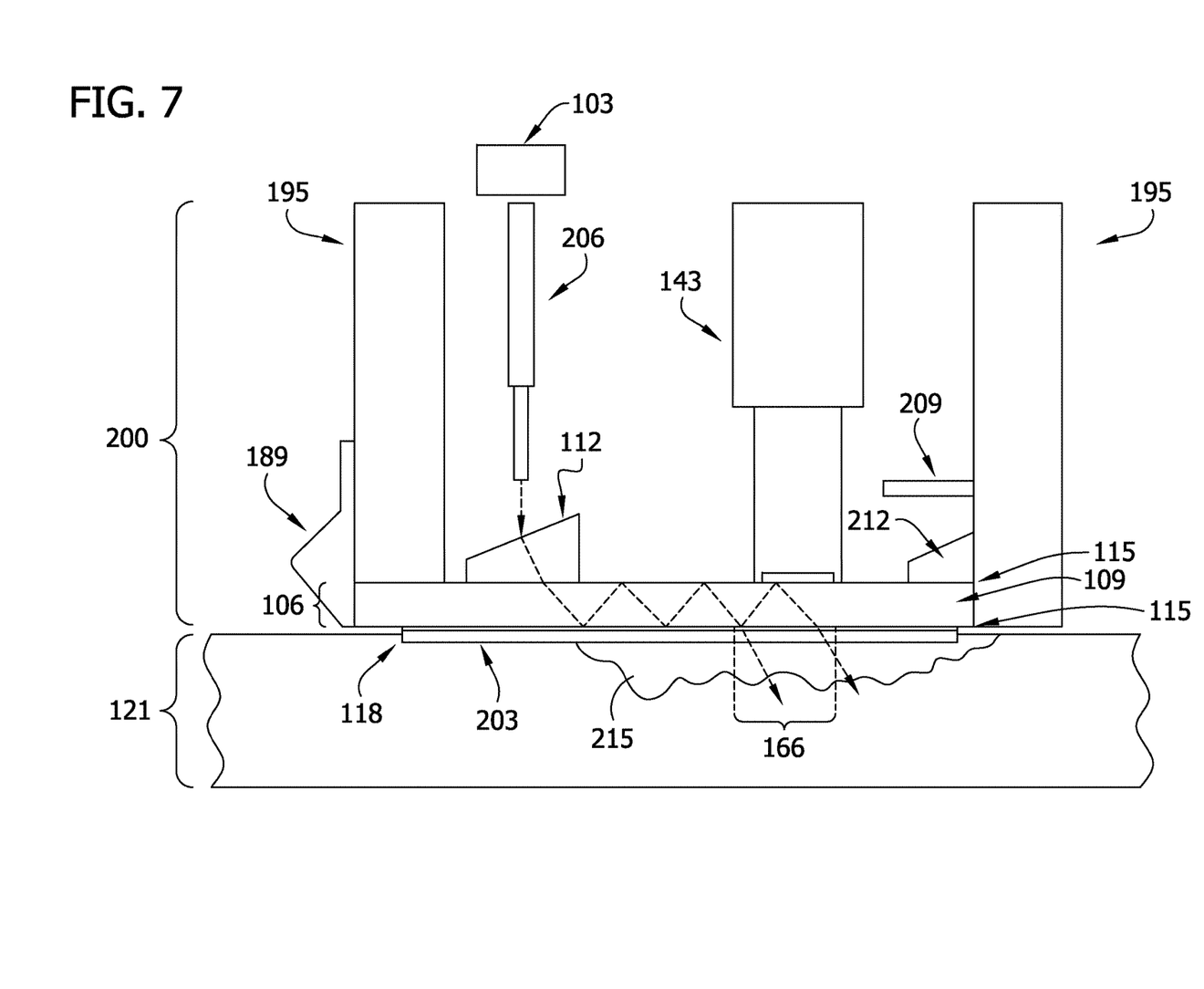
FIG. 7 illustrates an exemplary system for controlled delivery of an electromagnetic wave for use in sensing photoacoustic signals according to another embodiment of the invention.

FIG. 7 illustrates a cross sectional view of an exemplary system 200 for the controlled delivery of an electromagnetic wave for use in sensing photoacoustic signals according to an embodiment of the invention. Additionally or alternatively, the system 200 includes components suitable for the controlled delivery of an electromagnetic wave to target 121 at an intensity level suitable for ablation. The system 200 includes source 103 coupled to coupling lens 112. The source 103 is configured to transmit the wave to waveguide 106 using the coupling lens 112. The waveguide 106 comprises propagating medium 109 for transmitting an electromagnetic wave therethrough. The cladding 115 surrounds the propagating medium 109 and the interface 118 of cladding 115 is configured for controlled delivery of the wave to the target 121 when the interface 118 is in direct contact with target 121 having a sufficient refractive index. Housing 195 surrounds and encloses various components of system 200 as illustrated in FIG. 7. In an embodiment, housing 195 further comprises additional components uses in ablation and sensing, such as contact cooling elements, electrodes, and imaging modalities. In the illustrated embodiment, the system 200 further comprises a microfluidic flow cell 203 and the interface 118 is formed in part by direct contact between the microfluidic flow cell 203 and the target 121. In an embodiment, an acoustic response is detected in part based on interaction between the delivered wave and an additional sensing modality placed in front of the waveguide, such as sample 215. In an embodiment, the system 200 further comprises the slide lock 189 and ultrasonic sensor 143. In addition, system 200 includes an optical fiber 206 for transmitting the wave from the source 103 to the coupling lens 112 and a beam dump 209 for receiving the wave from an additional coupling lens 212 and for absorbing the energy of the wave after the wave propagates through the propagating medium 109.

With further reference to FIG. 7, the cladding 115 includes active area 166 scaled to control the energy of the wave that propagates into the target 121. Additionally, the relatively thick cladding 115 coating the remainder of the propagation medium 109 of waveguide apparatus 106 inhibits energy loss as the wave propagates along the medium 109.

According to aspects of the invention, the propagation medium 109 is optically transparent to the wavelengths of interest and chosen to have suitable thermal limits such that the optical damage threshold of the waveguide apparatus 160, measured in power output per square centimeter, does not serve as a limiting factor in high power ablation applications such as tattoo removal. In an embodiment, the propagation medium 109 is optically transparent to wavelengths of visible and near infrared light.

Additionally, the relatively thick cladding 115 coating the remainder of the propagation medium 109 of waveguide apparatus 160 inhibits energy loss as the wave propagates along the medium 109.

For example, the propagation medium 109 is comprised of an optically transparent glass, polymer, or crystal. In this regard, non-limiting examples of such material include fused silica, borosilicate glass such as N-BK7 glass, sapphire, and poly(methyl methacrylate) (PMMA). Additionally or alternatively, the propagation medium 109 comprises another type of fused silica for high power transmission.

In an embodiment, the cladding 115 surrounding the propagation medium 109 is composed of appropriate materials for use with electromagnetic waves comprising light in the visible spectrum. The cladding 115 is configured to have a low refractive index relative to the refractive index of the propagation medium 109. To configure the waveguide 106 with the direct-contact design described herein, the cladding 115 is at least partially transparent to the wavelength of the propagated wave. Non-limiting examples of such materials include microporous silica, mesoporous silica, zeolite thin films, Silver, Gold, Aluminum, and Titanium. In an embodiment, the cladding 115 is comprised of a polymer, resulting in a cladding 115 that readily adheres to most materials used for fabricating propagation medium 109.

In an alternative embodiment, the cladding 115 is a metal such as a reflective metal, resulting in reduced loss and a broadened range of acceptable internal reflection angles. In a further embodiment, an additional material is incorporated between the propagation medium 109 and the cladding 115 to provide a thin adhesion layer between the medium 109 and the cladding 115. One non-limiting example of such a material comprises titanium. Because silver does not readily adhere to propagation medium 109 composed of glass, a thin layer of titanium deposited between propagation medium 109 and the cladding 115 increases the adhesion between the materials. Additionally or alternatively, a third layer is deposited to thicken the cladding 115 to prevent a costly material (such as silver or gold, for example) from having to be deposited in substantial thickness.

The order of execution or performance of the operations in embodiments of the invention illustrated and described herein is not essential, unless otherwise specified. That is, it is envisioned that the operations are performed in any order in alternative embodiments, unless otherwise specified, and it is envisioned that embodiments of the invention include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A system for controlled delivery of an electromagnetic wave to a target comprising:
    a housing;
    a rectangular waveguide for receiving the electromagnetic wave from an electromagnetic source, the rectangular waveguide configured for sliding engagement in the housing, the rectangular waveguide comprising:
        a propagation medium coupled to the source for receiving the electromagnetic wave therefrom and configured to transmit the received electromagnetic wave therethrough; and
        a cladding surrounding the propagation medium;
        wherein the cladding has a lower refractive index relative to a refractive index of the propagation medium to cause the electromagnetic wave to be internally reflected within the propagating medium and to inhibit energy loss as the electromagnetic wave propagates within the propagation medium;
        wherein the cladding comprises an interface at a front surface of the rectangular waveguide, the cladding configured for direct physical contact with the target; and
        wherein the cladding is configured to permit a first portion of the electromagnetic wave to penetrate through the cladding at the interface and propagate into the target and to cause a second portion of the electromagnetic wave to be internally reflected such that the second portion of the electromagnetic wave continues to propagate within the propagating medium when the cladding is in direct physical contact with the target at the interface and the refractive index of the target at the interface is approximately the same as or greater than the refractive index of the propagating medium;
    a first coupling lens through which the electromagnetic source is coupled to the rectangular waveguide;
    an ultrasonic sensor positioned at a back surface of the rectangular waveguide and configured to receive photoacoustic signals incited in the target by the first potion of the electromagnetic wave, the ultrasonic sensor receiving the photoacoustic signals along the same axis as the first portion of the electromagnetic wave propagated into the target;
    a beam dump for absorbing energy of the second portion of the electromagnetic wave after the electromagnetic wave propagates through the propagation medium; and
    a second coupling lens through which the propagation medium is coupled to the beam dump.

2. The system of claim 1, wherein the rectangular waveguide is configured to receive the electromagnetic wave when the electromagnetic wave has an intensity level suitable for ablation.

3. The system of claim 2, further comprising an ultrasonic pulser for increasing the penetration depth of the electromagnetic wave propagated into the target.

4. The system of claim 1, wherein the rectangular waveguide is configured to receive the electromagnetic wave when the electromagnetic wave has an intensity level suitable for detecting photoacoustic waves incited in the target.

5. The system of claim 1, wherein the propagation medium comprises a slab.

6. The system of claim 1, wherein the propagation medium comprises at least one of the following: an optically transparent glass, a polymer, and a crystal.

7. The system of claim 1, wherein the cladding comprises a material having a low refractive index relative to the propagation medium.

8. The system of claim 1, wherein the cladding comprises at least one of a metal and a polymer.

9. The system of claim 1, wherein the cladding comprises an active area scaled to control the energy of the first portion of the electromagnetic wave that propagates into the target through the cladding at the interface.

10. The system of claim 9, wherein the active area comprises a thin film formed by at least one of: mesoporous silica, zeolites, silver, titanium, and molybdenum.

11. The system of claim 9, wherein the active area comprises a thin section of the cladding relative to other sections of the cladding on the remainder of the rectangular waveguide, thereby allowing an evanescent field formed by internal reflection of the propagated electromagnetic wave to penetrate into an external medium surrounding the rectangular waveguide; and wherein the relatively thick other sections of cladding on the remainder of the rectangular waveguide inhibits energy loss.

12. A method comprising:
    coupling an electromagnetic source to a rectangular waveguide through a first coupling lens;
    receiving, by the rectangular waveguide, an electromagnetic wave from the electromagnetic source, the rectangular waveguide configured for sliding engagement in a housing and comprising:
        a propagation medium coupled to the source for receiving the electromagnetic wave therefrom and configured to transmit the received electromagnetic wave therethrough; and a cladding surrounding the propagation medium, the cladding comprising an interface configured for direct physical contact with the target, wherein the cladding has a lower refractive index relative to a refractive index of the propagation medium to cause the electromagnetic wave to be internally reflected within the propagating medium and to inhibit energy loss as the electromagnetic wave propagates within the propagation medium, and wherein the cladding comprises an interface at a front surface of the rectangular waveguide, the cladding configured for direct physical contact with the target;

propagating the electromagnetic wave within the propagation medium when the refractive index at the interface of the cladding is less than that of the propagation medium;

propagating a first portion of the electromagnetic wave into the target by penetrating through the cladding at the interface when the cladding is in direct physical contact with the target at the interface and the refractive index of the target at the interface is approximately the same as or greater than the refractive index of the propagation medium, wherein a second portion of the electromagnetic wave is internally reflected such that the second portion of the electromagnetic wave continues to propagate within the propagating medium when the cladding is in direct physical contact with the target at the interface and the refractive index of the target at the interface is approximately the same as or greater than the refractive index of the propagating medium;

receiving, by an ultrasonic sensor positioned at a back surface of the rectangular waveguide, photoacoustic signals incited in the target by the first portion of the electromagnetic wave, wherein the ultrasonic sensor receives the photoacoustic signals along the same axis as the first portion of the electromagnetic wave propagated into the target;

absorbing, by a beam dump, energy of the second portion of the electromagnetic wave after the electromagnetic wave propagates through the propagation medium; and coupling the propagation medium to the beam dump through a second coupling lens; and defining an active area in the cladding scaled to control the energy of the first portion of the electromagnetic wave that propagates into the target through the cladding at the interface.

13. The method of claim 12, wherein the electromagnetic wave has an intensity level suitable for ablation.

14. The method of claim 13, further comprising providing ultrasonic pulses to the target for increasing the penetration depth of the electromagnetic wave propagated into the target.

15. The method of claim 12, wherein the electromagnetic wave has an intensity level suitable for detecting photoacoustic waves incited in the target.

16. The method of claim 12, further comprising cooling the target.

17. The method of claim 12, wherein the propagation medium comprises a slab.

* * * * *